United States Patent
Georgeson et al.

(10) Patent No.: US 9,658,173 B2
(45) Date of Patent: May 23, 2017

(54) PORTABLE X-RAY BACKSCATTERING IMAGING SYSTEM INCLUDING A RADIOACTIVE SOURCE

(71) Applicant: The Boeing Company, Chicago, IL (US)

(72) Inventors: Gary Georgeson, Tacoma, WA (US); Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 273 days.

(21) Appl. No.: 14/447,145

(22) Filed: Jul. 30, 2014

(65) Prior Publication Data

US 2016/0033426 A1 Feb. 4, 2016

(51) Int. Cl.
*G01V 5/00* (2006.01)
*G01N 23/203* (2006.01)

(52) U.S. Cl.
CPC ......... *G01N 23/203* (2013.01); *G01V 5/0025* (2013.01); *G01N 2223/301* (2013.01); *G01N 2223/631* (2013.01)

(58) Field of Classification Search
CPC ........... G01N 23/203; G01N 2223/301; G01V 5/0025
See application file for complete search history.

(56) References Cited

U.S. PATENT DOCUMENTS

| | | | |
|---|---|---|---|
| 4,494,001 A * | 1/1985 | Peck | G01N 23/203 250/358.1 |
| 7,463,714 B2 | 12/2008 | Edwards et al. | |
| 7,508,910 B2 | 3/2009 | Safai et al. | |
| 7,529,343 B2 | 5/2009 | Safai et al. | |
| 7,599,471 B2 | 10/2009 | Safai et al. | |
| 7,623,626 B2 | 11/2009 | Safai et al. | |
| 7,649,976 B2 | 1/2010 | Georgeson et al. | |
| 8,033,724 B2 | 10/2011 | Edwards et al. | |
| 8,094,781 B1 | 1/2012 | Safai et al. | |
| 2010/0327174 A1* | 12/2010 | Edwards | G01N 23/203 250/370.09 |
| 2013/0195248 A1* | 8/2013 | Rothschild | G01N 23/203 378/86 |

OTHER PUBLICATIONS

U.S. Appl. No. 14/258,432, filed Apr. 22, 2014, Georgeson et al.
(Continued)

*Primary Examiner* — Dani Fox
(74) *Attorney, Agent, or Firm* — Thompson Hine LLP

(57) ABSTRACT

A portable x-ray backscattering imaging system for creating a backscatter image representing an object is disclosed. The portable x-ray backscattering imaging system may include a drum, a radioactive source, a plurality of backscatter detectors, and a portable exterior shield. The drum may be rotatable about an axis of rotation at a rotational speed. The radioactive source may be connected to the drum and configured to generate x-rays. The plurality of backscatter detectors may be configured to detect backscattering radiation created as the x-rays generated by the radioactive source scatter back from the object. The portable exterior shield may enclose the drum. The exterior shield may be constructed of a material that substantially blocks the x-rays and defines a window that allows for the x-rays to pass through.

19 Claims, 7 Drawing Sheets

(56) References Cited

OTHER PUBLICATIONS

U.S. Appl. No. 14/269,930, filed May 5, 2014, Grimshaw et al.
U.S. Appl. No. 14/272,177, filed May 7, 2014, Edwards et al.
Watson, Paul Joseph, "Police to Get X-Ray Scanner for Vehicle Inspections & 'Public Safety,'" website of Infowars, http://www.infowars.com/police-to-get-x-ray-scanner-for-vehicle-inspections-public-safety/ (Jun. 23, 2014).
Addicott, Benjamin Teichman, Characterization and Optimization of Radiography by Selective Detection Backscatter X-Ray Imaging Modality,: A Thesis Presented to the Graduate School of the University of Florida in Partial Fulfillment of the Requirements for Degree of Master of Engineering, University of Florida, pp. i-222 (2006).

* cited by examiner

PORTABLE X-RAY BACKSCATTERING IMAGING SYSTEM INCLUDING A RADIOACTIVE SOURCE

FIELD

The disclosed system relates to a portable x-ray backscattering imaging system and, more particularly, to a portable x-ray backscattering imaging system including a radioactive source for generating x-rays.

BACKGROUND

It is often necessary to inspect internal components of various types of objects, such as buildings, automobiles, containers, aircraft, or maritime vessels. Inspection of such structures and facilities by partial or complete disassembly of the structures to visually inspect internal components of interest may be impracticable.

One technique for inspecting such components utilizes x-ray backscattering imaging systems. X-ray backscattering imaging systems provide an inspection process in which x-rays are reflected backwards from within the object or component of interest and recorded by a detector or detectors. X-ray backscattering imaging systems do not need to be powerful enough to transmit x-rays entirely through the component of interest and its surrounding components. Rather, partial penetration to a depth of interest is all that is required. However, traditional x-ray backscattering imaging systems are often large and cumbersome. Therefore, traditional x-ray back scattering systems may be impractical for an individual to use in some types of situations where a portable, hand-held device is required. For example, a border patrol officer may require a portable device to inspect the doors and sides of a vehicle for hidden contraband. In another example, a building contractor or other individual may require a portable device to rapidly inspect the walls of a building for internally located structures such as pipes or electrical cables.

There are some portable devices currently available that allow a user to inspect features or characteristics of an object. Some examples of these portable devices include ultrasonic arrays, infrared cameras, and terahertz cameras. Although all of these portable devices are relatively easy to transport and are hand-held, they still have various other limitations. For example, these types of portable devices may only be used to inspect single layer structures or structures where there is not a continuity of materials (i.e., where there are air gaps). Thus, there exists a continuing need in the art for an improved x-ray backscattering imaging system that is relatively lightweight and portable.

SUMMARY

In one aspect, a portable x-ray backscattering imaging system for creating a backscatter image representing an object is disclosed. The portable x-ray backscattering imaging system may include a drum, a radioactive source, a plurality of backscatter detectors, and a portable exterior shield. The drum may be rotatable about an axis of rotation at a rotational speed. The radioactive source may be connected to the drum and configured to generate x-rays. The plurality of backscatter detectors may be configured to detect backscattering radiation created as the x-rays generated by the radioactive source scatter back from the object. The portable exterior shield may enclose the drum. The exterior shield may be constructed of a material that substantially blocks the x-rays and defines a window that allows for the x-rays to pass through.

In yet another aspect, a method of creating a backscatter image representing an object is disclosed. The method includes generating x-rays by a radioactive source, where the radioactive source may be connected to a drum. The method also includes rotating the drum about an axis of rotation at a rotational speed. The method further includes detecting backscatter radiation by a plurality of backscatter detectors. The backscatter radiation may be created as the x-rays generated by the radioactive source scatter back from the object. The method also includes enclosing the drum by a portable exterior shield. The exterior shield may be constructed of a material that substantially blocks the x-rays and defines a window that allows for the x-rays to pass through. Finally, the method includes generating the backscatter image on a display by a controller. The controller may be in signal communication with the plurality of backscatter detectors and the display.

Other objects and advantages of the disclosed method and system will be apparent from the following description, the accompanying drawings and the appended claims.

DETAILED DESCRIPTION

Figure 1:
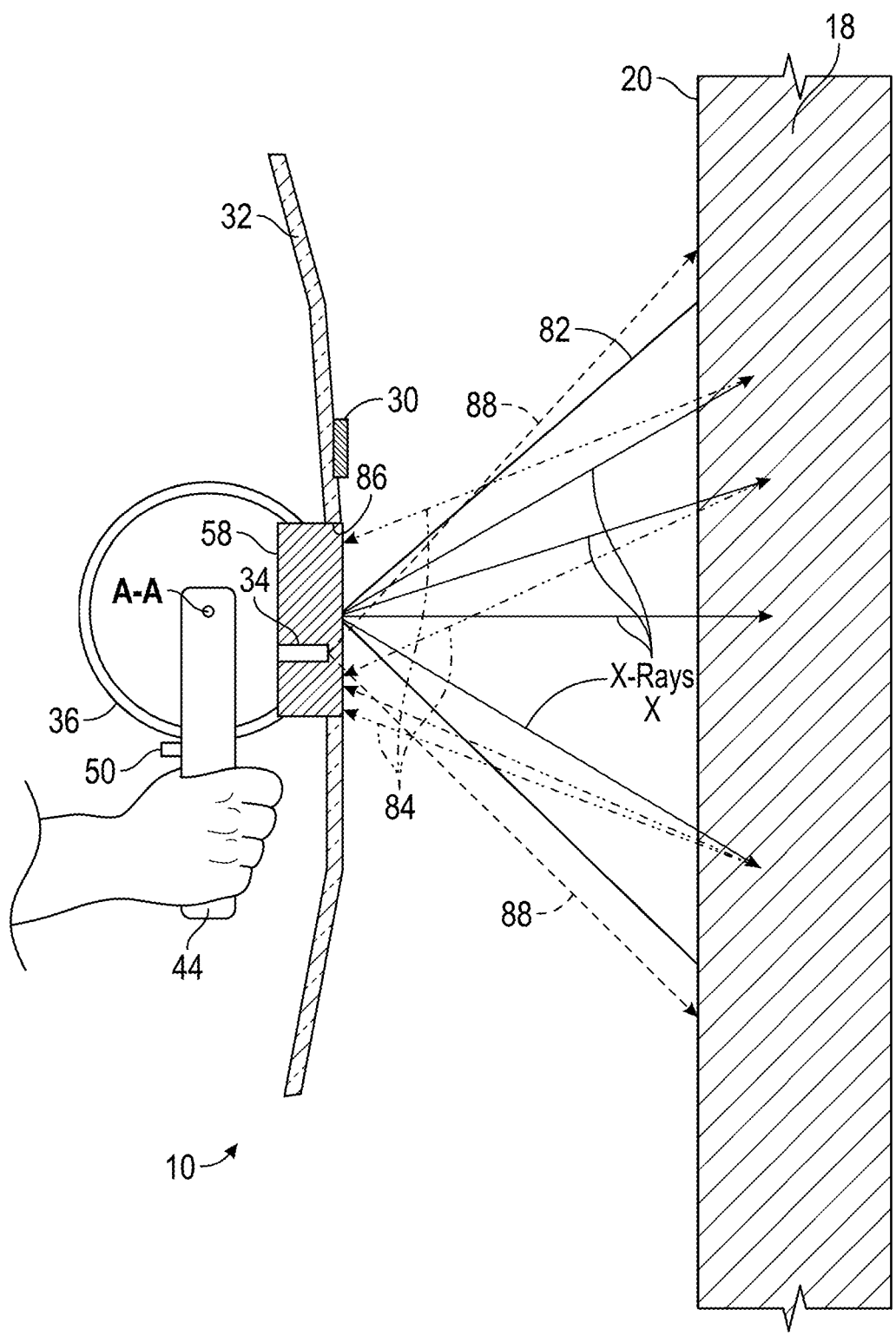
FIG. 1 is a schematic illustration of an exemplary portable x-ray backscattering imaging system for inspecting a structure.

As shown in FIG. 1, the disclosed portable x-ray backscattering imaging system 10 according to an aspect of the disclosure may be used to non-destructively inspect an object or structure 18. In one approach, the structure 18 may be a multilayer object such as, for example, a building. As explained in greater detail below, an operator may move the portable x-ray backscattering imaging system 10 in a generally horizontal direction with respect to the structure 18 in order to inspect one or more areas of the structure 18. The horizontal movement of the portable x-ray backscattering imaging system 10 may be tracked by an on-board positioning system 30. In the example as shown in FIG. 1, the portable x-ray backscattering imaging system 10 may include the on-board positioning system 30, a front shield 32, a x-ray field of view (FOV) marker 34, an exterior shield 36, a rotating drum 40 (shown in FIG. 4A), a radioactive source 42 (shown in FIG. 4A), a handle 44, a safety device 50, and one or more backscatter detectors 58.

Figure 2:
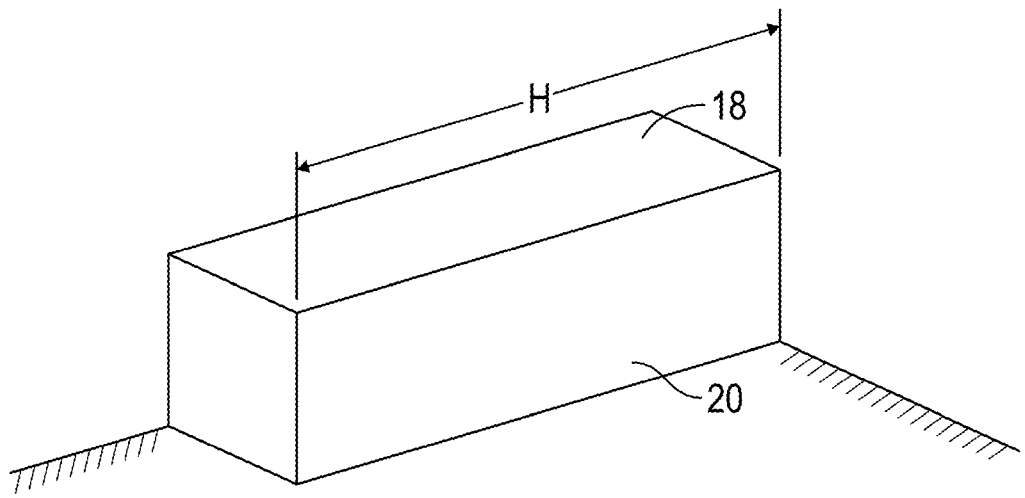
FIG. 2 is a perspective view of the structure shown in FIG. 1.

The on-board positioning system 30 may be any type of device for detecting and measuring the horizontal displacement of the x-ray backscattering imaging system 10 in a horizontal direction H with respect to the structure 18 (seen in FIG. 2). For example, the on-board positioning system 30 may be an inertial measuring unit (IMU), a global positioning system (GPS), at least one acoustic distance sensor, an optical encoder configured to read an exterior surface 20 of the structure 18, one or more encoder wheels that roll against the exterior surface 20 of the structure 18, or one or more linear encoders.

Figure 3:
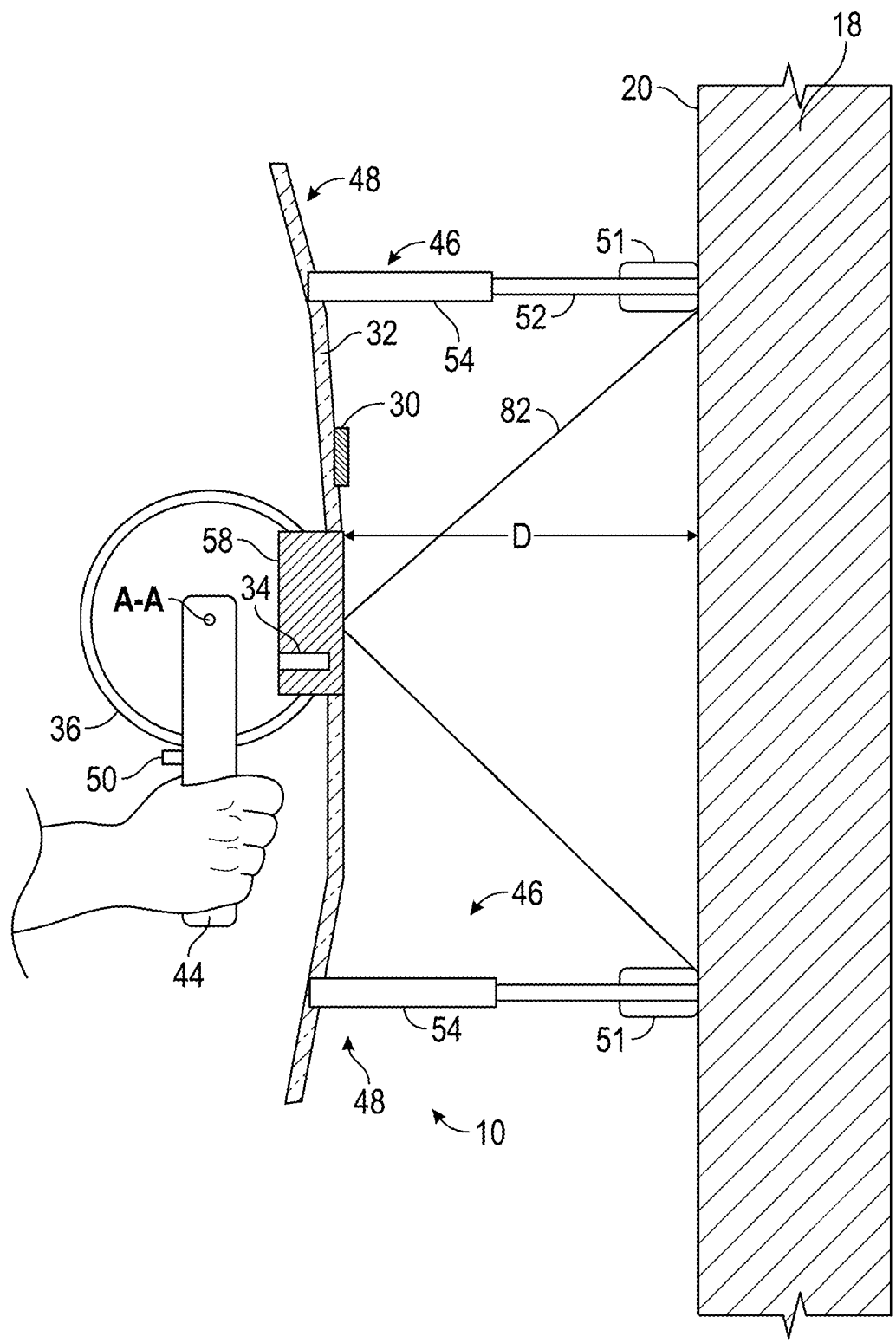
FIG. 3 is a schematic illustration of the portable x-ray backscattering imaging system shown in FIG. 1 including telescopic wheeled standoffs.

In one non-limiting approach as seen in FIG. 3, the x-ray backscattering imaging system 10 may also include one or more telescopic standoffs 46. The telescopic standoffs 46 may be advantageously used to maintain a fixed distance D between the x-ray backscattering imaging system 10 and the exterior surface 20 of the structure 18 as the operator moves the portable x-ray backscattering imaging system 10 in the horizontal direction H along the structure 18 (FIG. 2). Specifically, in the illustration as shown, two telescopic standoffs 46 are each oriented at a vertical end 48 of the x-ray backscattering imaging system 10. Each telescopic standoff 46 may include a roller element or wheel 51 that rolls or translates against the exterior surface 20 of the structure 18. In one example, the wheels 51 may be motorized to provide a controlled transverse speed. The telescopic standoffs 46 may also include a stem 52 that may telescope in and out of a receiving cylinder 54. The stem 52 may move in or out of the cylinder 54 in order to adjust the distance D between the x-ray backscattering imaging system 10 and the exterior surface 20 of the structure 18.

Figure 4A:
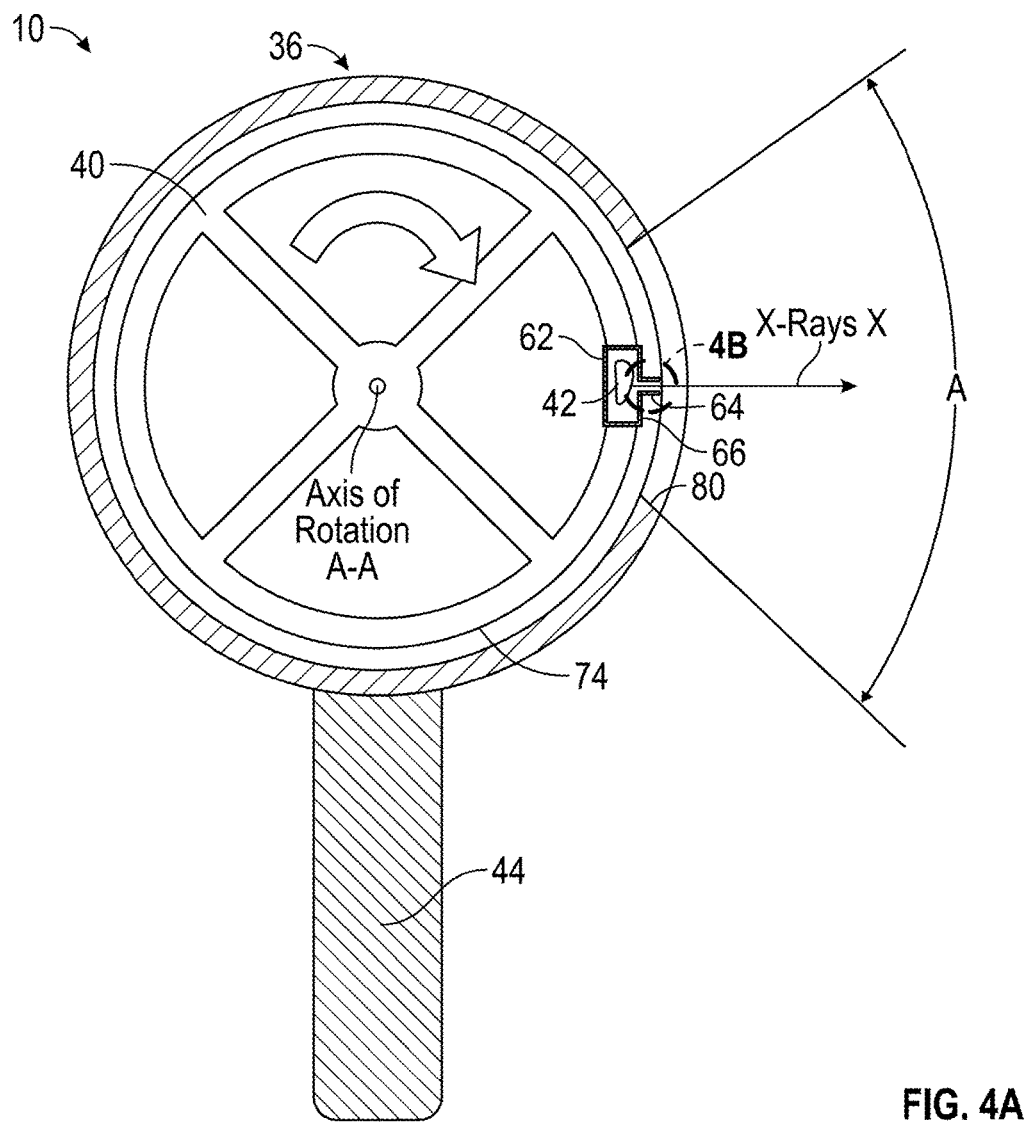
FIG. 4A is a side cross-sectioned view of the portable x-ray backscattering imaging system shown in FIG. 1.

Turning to FIG. 4A, in one approach the radioactive source 42 may be a gamma source that emits gamma radiation. Some examples of gamma sources include, but are not limited to, Cesium-137, Cobalt-60, and Iridium-192. Some other types of radioactive elements that may be used include, for example, alpha sources, beta sources, or neutron sources. The radioactive source 42 may be housed within a container 62. The radioactive source 42 may be relatively small and lightweight, thereby enabling the disclosed x-ray backscattering imaging system 10 to be portable and easily held by a user. For example, in one approach the radioactive source may weigh less than about 28.3 grams (about 1 ounce), and the x-ray backscattering imaging system may weigh between about 0.9 to about 2.2 kilograms (about 2-5 pounds).

Figure 4B:
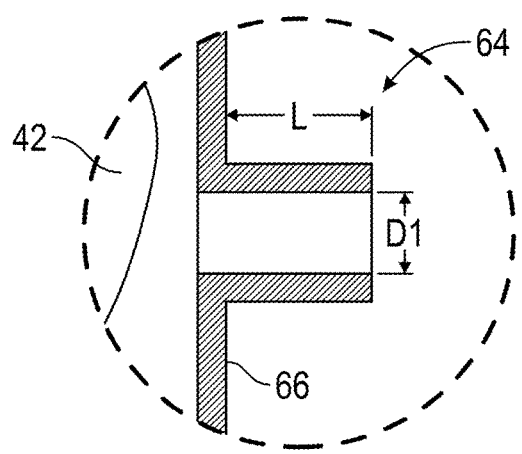
FIG. 4B is an enlarged view of a collimator shown in FIG. 4A.

The container 62 may be constructed of a relatively dense material and may substantially shield or stop the radiation generated from the radioactive source 42 from exiting the container 62 such as, for example, lead or tungsten. The container 62 may be used to contain the radioactive source 42 therein. The container 62 may define a collimator 64 located along an outermost edge or face 66 of the container 62. FIG. 4B is an enlarged view of the collimator 64 shown in FIG. 4A. The collimator 64 may define a length L and an aperture opening diameter D1. In one non-limiting approach, the aperture opening W may range in dimension from about a quarter of a millimeter to about three millimeters. The collimator 64 may be used to collimate the radiation generated by the radioactive source 42. Specifically, the collimator 64 filters a stream of x-rays generated by the radioactive source 42 such that only the x-rays traveling substantially parallel with respect to the length L of the collimator 64 may be allowed to pass through.

Figure 7:
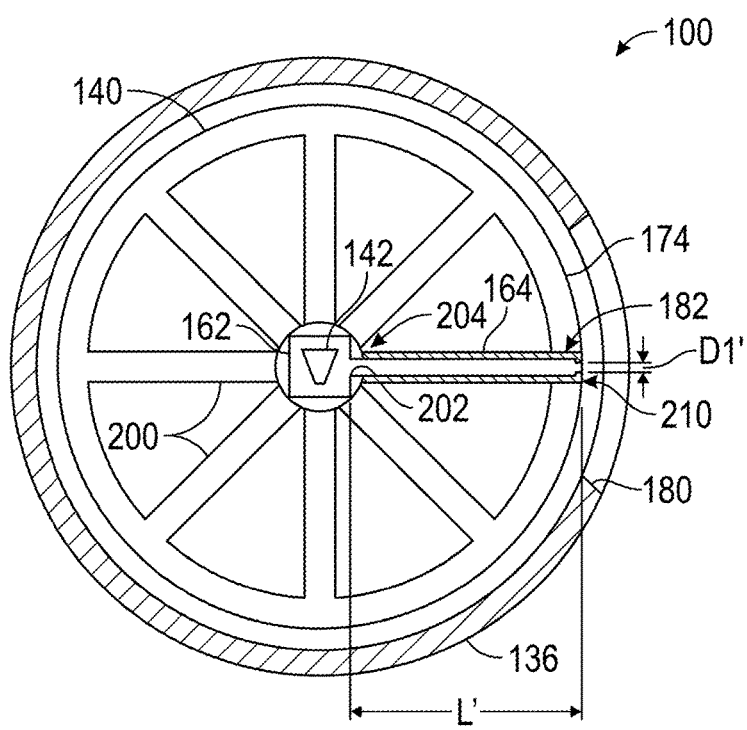
FIG. 7 is an alternative illustration of the portable x-ray backscattering imaging system shown in FIG. 1, with a radioactive source placed within a rotating drum having a single collimator and multiple spokes.

Referring to FIG. 4A, the container 62 may be connected to the drum 40. The drum 40 may be housed or encased within the exterior shield 36, and rotates about an axis of rotation A-A. In the non-liming example as shown, the exterior shield 36 may include a generally cylindrical profile. The exterior shield 36 and the drum 40 may both be sized such that they are relatively lightweight and portable, and an operator may easily carry or hold the x-ray backscattering imaging system 10 using the handle 44. In the illustration as shown in FIG. 4A, the container 62 may be located along an outermost surface 74 of the drum 40. However, in an alternative approach, the container 62 may also be housed within the drum 40 as well, which is illustrated in FIG. 7 and described in greater detail below. However, placing the container 62 at the outermost surface 74 of the drum 40 may allow for a greater flux density, which results in a faster scan of the structure 18 (FIG. 1). For example, the drum 40 may rotate at any predetermined speed ranging from about 10 revolutions per second to about one-tenth of a revolution per second. The exact predetermined speed may depend on a specified or desired vertical image contrast resolution of a two-dimensional backscatter image generated by the x-ray backscattering imaging system 10. For example, a faster predetermined speed may result in a lower resolution backscatter image.

The x-rays generated by the radioactive source 42 may travel through a scanning window 80, which is an opening defined by the exterior shield 36. The exterior shield 36 may be constructed of a relatively dense material having a high atomic number that may substantially shield or stop the radiation generated from the radioactive source 42 such as, for example, titanium or lead. The scanning window 80 may be constructed of a material that allows for x-rays X (seen in FIG. 1) exiting the collimator 64 to pass through. The scanning window 80 may also be used to filter out lower energy x-rays from the x-rays X exiting the collimator 64. In one non-limiting example, the scanning window 80 may be constructed of a relatively thin sheet of aluminium or copper having a thickness ranging from about one-tenth a millimeter to about five millimeters. In another approach, the scanning window 80 may be an open void within the exterior shield 36. As seen in FIG. 4A, the scanning window 80 may be formed as an angle A around the exterior shield 36. In one approach, the angle A may range from about ten degrees to about one hundred and twenty degrees with respect to the axis of rotation A-A of the drum 40. The specific dimensions of the angle A may depend on a desired height of the backscatter image generated by the x-ray backscattering imaging system 10. For example, a smaller angle A results in a shorter backscatter image, while a larger angle A results in a taller backscatter image.

As the drum 40 rotates during operation of the x-ray backscattering imaging system 10, the x-rays X exiting the collimator 64 may selectively pass through the scanning window 80 within the exterior shield 36 at a specific frequency, and may be directed towards the structure 18 (FIG. 1). Specifically, with reference to both FIGS. 1 and 4A, the x-rays may be directed onto the structure 18 to define an x-ray FOV 82 upon the structure 18. The x-ray FOV 82 defines where the x-rays generated by the x-ray backscattering imaging system 10 are focused upon the structure 18.

Referring to FIG. 1, the FOV marker 34 may be used to provide a visual indictor or marker 88 upon the exterior surface 20 of the structure 18 generally indicating the x-ray FOV 82. Thus, the operator may be able to easily see where the x-rays generated by the x-ray backscattering imaging system 10 are focused. In one non-limiting example, the FOV marker 34 may be a laser diode used to generate a beam of visible light against the exterior surface 20 of the structure 18. The front shield 32 may be used as a safety device, and generally protects an operator from backscattering radiation 84 created as the x-rays generated by the x-ray backscattering imaging system 10 scatter back from the structure 18.

The shield 32 may define an aperture or opening 86. Referring to both FIGS. 1 and 4A, the x-rays exiting the scanning window 80 within the exterior shield 36 may pass through the opening 86 of the shield 32 and towards the structure 18. The shield 32 may be constructed from any type of relatively dense material that may substantially shield or stop the radiation generated from the radioactive source 42 from reaching the operator such as, for example, lead, iron, ceramics, or tungsten.

Figure 5:
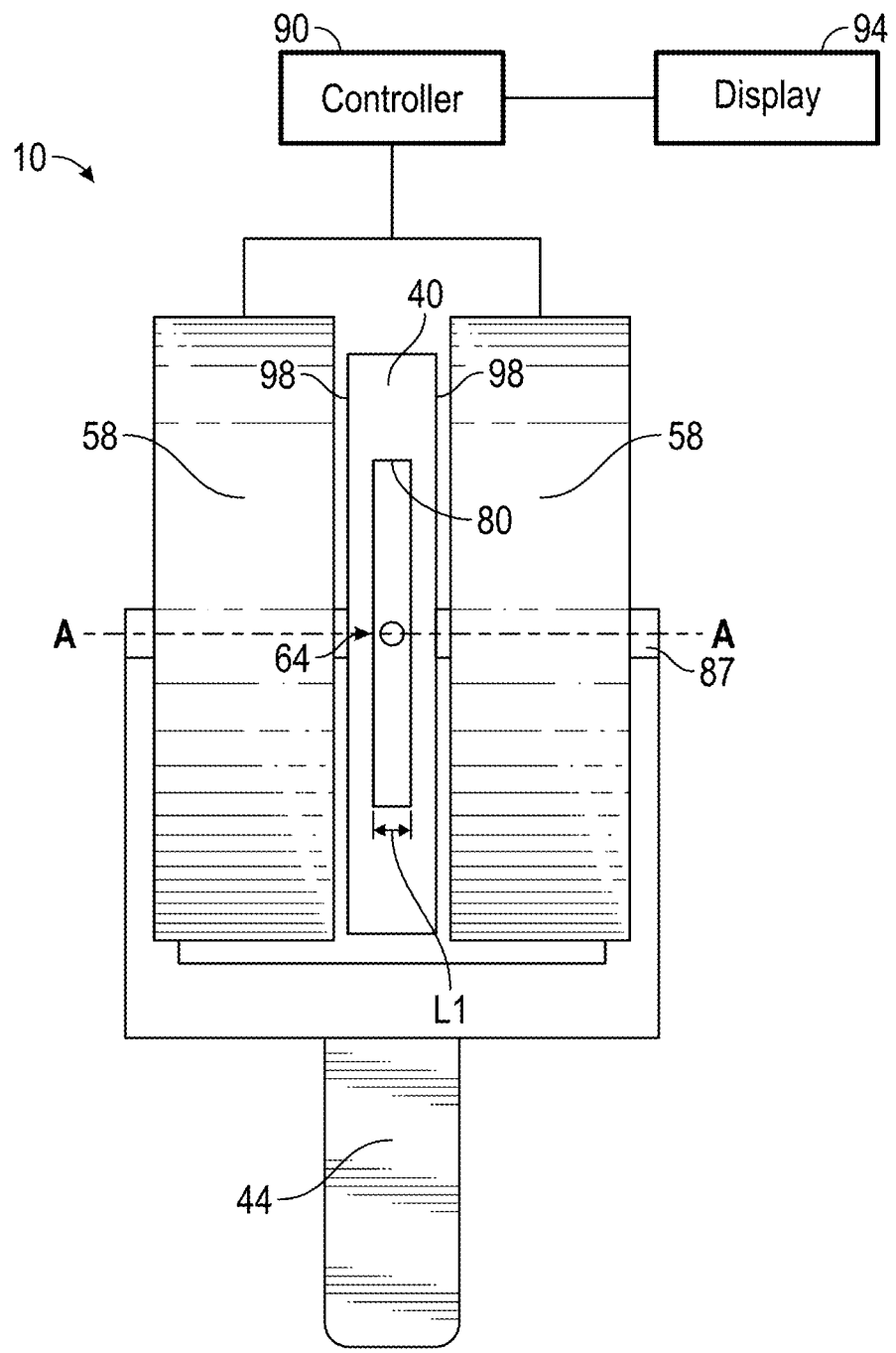
FIG. 5 is a front schematic view of the portable x-ray backscattering imaging system, where a shield has been removed.

FIG. 5 is a front view of the x-ray backscattering imaging system 10, where the handle 44, the drum 40, and the backscatter detectors 58 are illustrated (the front shield 32 has been removed in FIG. 5). As seen in FIG. 5, the scanning window 80 may include a horizontal length L1. The horizontal length L1 of the scanning window 80 should be sized to be at least as wide as the aperture opening diameter D1 of the collimator 64 (shown in FIG. 4B).

Continuing to refer to FIG. 5, the handle 44 may be rotatably attached to the drum 40. Specifically, the handle 44 may include a rod 87 located along the axis of rotation A-A of the drum 40. In the example as illustrated in FIG. 5, a backscatter detector 58 is located on opposing sides 98 of the drum 40. The backscatter detectors 58 may generate a signal based on the backscattering radiation 84 detected. The backscatter detectors 58 may be, for example, solid state detectors or scintillators.

The x-ray backscattering imaging system 10 may also include a controller 90 in signal communication with a display 94. The controller 90 may also be in signal communication with backscatter detectors 58 as well as the on-board positioning system 30 shown in FIG. 1. The controller 90 may refer to, or be part of, an application specific integrated circuit (ASIC), an electronic circuit, a combinational logic circuit, a field programmable gate array (FPGA), a processor (shared, dedicated, or group) that executes code, or a combination of some or all of the above, such as in a system-on-chip. The controller 90 may include control logic for generating the backscatter image representing an interior and/or an opposing side of the structure 18 (FIG. 1) upon the display 94. The backscatter image may be based on a position signal received from the on-board positioning system 30. The position signal may indicate horizontal position information relating to the location of the x-ray backscattering imaging system 10 relative to the structure 18 as the x-ray backscattering imaging system 10 is moved in the horizontal direction H (FIG. 2).

Referring to both FIGS. 1 and 5, the controller 90 may include control logic for correlating the movement of the x-ray backscattering imaging system 10 in the horizontal direction H as well as a vertical scan movement of the radioactive source 42 with a density of the x-ray backscatter 84 detected by the backscatter detectors 58. The controller 90 may also include control logic for determining the backscatter image based on the horizontal direction H, the vertical scan movement of the radioactive source 42, and the density of the of the x-ray backscatter 84 detected by the backscatter detectors 58. The vertical scan movement of the radioactive source 42 may be defined based on an angle of the x-rays X exiting the collimator 64 as well as a distance the x-rays X exiting the collimator 64 may travel before being backscattered by the structure 18.

FIGS. 1, 3 and 5 illustrate the x-ray backscattering imaging system 10 in a first, in-use position, where the handle 44 may be oriented in a generally vertical direction. The x-ray backscattering imaging system 10 generates the backscatter image upon the display 94 in the in-use position as the x-ray backscattering imaging system 10 is moved in the horizontal direction H along the structure 18 (FIG. 2). Moreover, when the x-ray backscattering imaging system 10 is in the in-use position the safety device 50 (FIGS. 1 and 3) may be activated. The safety device 50 provides an indication to the operator that the x-ray backscattering imaging system 10 is emitting x-rays. The safety device 50 may be any type of mechanism for providing a visual, audio, or tactile indictor to an operator. For example, in one approach the safety device 50 may be a light.

Figure 6:
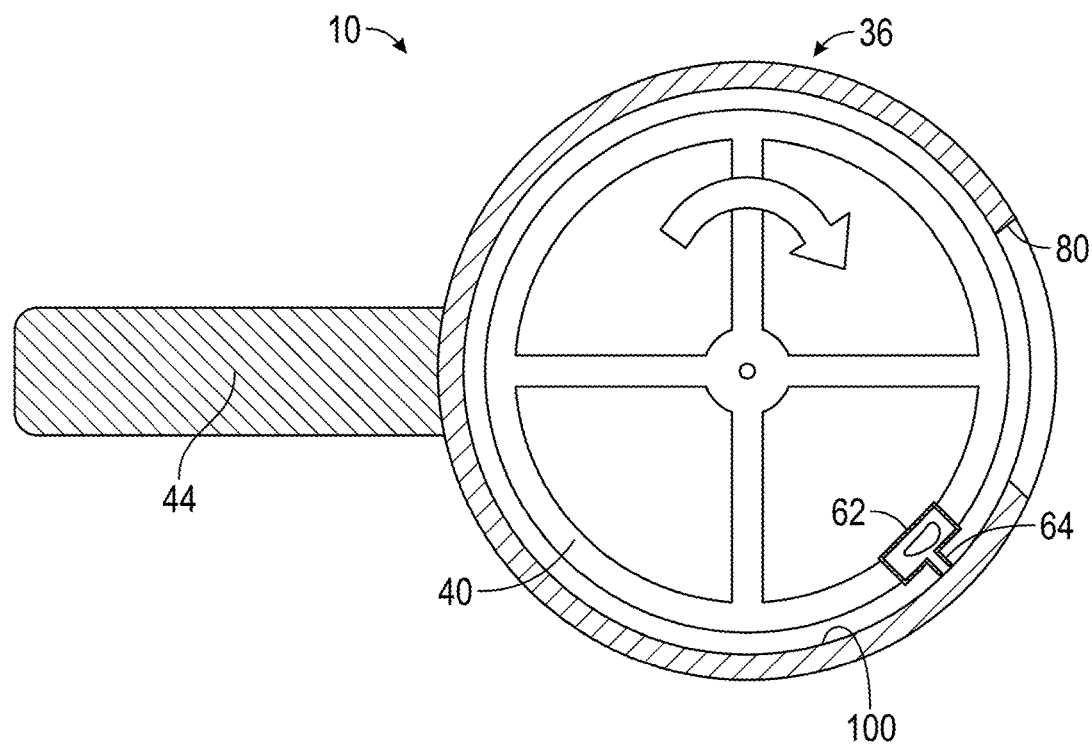
FIG. 6 is an illustration of the portable x-ray backscattering imaging system shown in FIG. 4A in a second, parked position.

FIG. 6 is an illustration of the x-ray backscattering imaging system 10 in a second, parked position, where the handle 44 has been rotated about ninety degrees and may be oriented in a generally horizontal direction. As seen in FIG. 6, when the x-ray backscattering imaging system 10 is in the parked position, the drum 40 has been rotated within the exterior shield 36 such that an interior surface 100 of the exterior shield 36 blocks the collimator 64. Thus, when the x-ray backscattering imaging system 10 is in the parked position, the x-rays X exiting the collimator 64 (seen in FIG. 4A) may not exit through the scanning window 80. In other words, the x-ray backscattering imaging system 10 does not emit x-ray radiation.

FIG. 7 is an alternative illustration of an x-ray backscattering imaging system 100, where a container 162 may be placed in a central location within a rotating wheel or drum 140. Similar to illustrations as shown in FIG. 4A, the container 162 may also be used to contain a radioactive source 142 therein. The drum 140 may include a plurality of spokes 200 as well as a collimator 164. The container 162 defines an interior opening or aperture 202. A first end 204 of the collimator 164 is connected to the aperture 202 within the container 162. A second, distal end 210 of the collimator 164 terminates along an outermost surface 174 of the drum 140. The collimator 164 may be used to collimate the radiation generated by the radioactive source 142. The collimator 164 may define a length L' as well as an aperture opening diameter D1'. The aperture opening diameter D1' may be defined by a narrowed opening 182 located on the distal end 210 of the collimator 164. The x-rays generated by the radioactive source 142 may selectively travel through a scanning window 180, which may be an opening defined by an exterior shield 136, and exits the x-ray backscattering imaging system 100.

Figure 8:
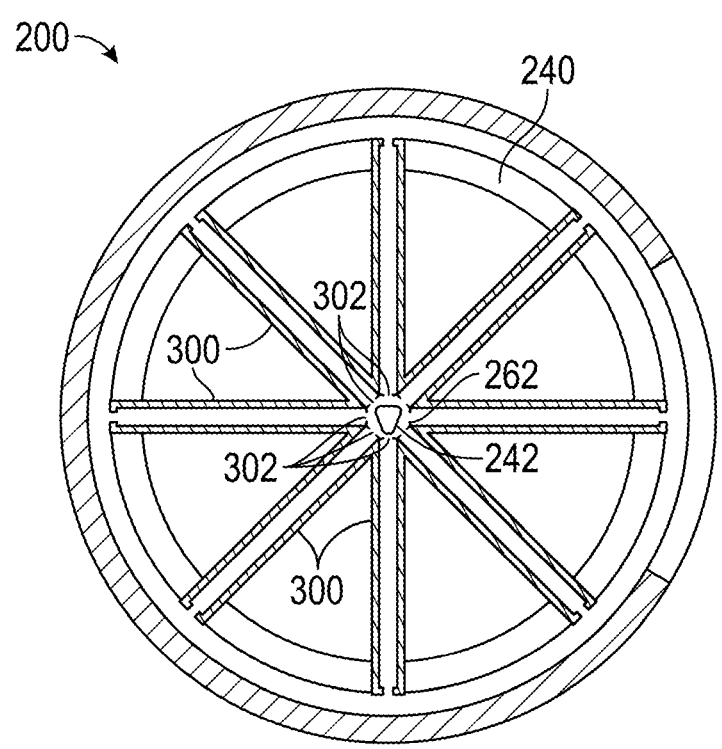
FIG. 8 is yet another alternative illustration of the portable x-ray backscattering imaging system shown in FIG. 1, with a rotating drum having multiple spokes that each act as a collimator.

In one approach, the drum 140 may include multiple collimators. FIG. 8 is an illustration of an x-ray backscattering system 200 where each spoke 300 of a drum 240 may define a collimator. Specifically, a container 262 may define a plurality of openings or apertures 302, where each aperture 302 may be connected to one of the spokes 300 of the drum 240. Those skilled in the art will readily appreciate that since the radioactive source 242 may emit x-rays radially in all directions (i.e., three hundred and sixty degrees), providing more than one collimator spoke may actually increase the vertical scan speed without increasing the rotational speed of the drum 240.

Referring generally to FIGS. 1-8, the disclosed portable x-ray backscattering imaging system is a portable, lightweight device that may be used to quickly inspect multilayer objects, such as a building wall. The disclosed backscattering imaging system may be used in a variety of applications where a portable device is required such as, for example, border patrol to inspect vehicles for contraband, or during warfare where military personnel may need to rapidly scan the walls of a building. The portable x-ray backscattering imaging system may be used to create a backscatter image representing an interior or an opposing side of a structure. Those skilled in the art will readily appreciate that the disclosed radiation source may provide a relatively compact and lightweight approach for generating x-rays, especially when compared to other known approaches for generating radiation such as an x-ray tube. Because the radiation source is relatively small and lightweight, this enables the disclosed portable x-ray backscattering imaging system to be a handheld device that may be easily manipulated by a user.

While the forms of apparatus and methods herein described constitute preferred aspects of this disclosure, it is to be understood that the disclosure is not limited to these precise forms of apparatus and methods, and the changes may be made therein without departing from the scope of the disclosure.

What is claimed is:

1. A portable x-ray backscattering imaging system for creating a backscatter image representing an object, comprising:
    a drum rotatable about an axis of rotation at a rotational speed;
    a radioactive source connected to the drum, the radioactive source for generating x-rays;
    a container housing the radioactive source, the container constructed of a material that substantially blocks the x-rays generated by the radioactive source, the container defining a collimator having a length and an aperture opening, wherein the collimator filters a stream of x-rays generated by the radioactive source such that the x-rays traveling substantially parallel with respect to the length of the collimator pass the aperture;
    a plurality of backscatter detectors for detecting backscattering radiation created as the x-rays generated by the radioactive source scatter back from the object; and
    a portable exterior shield to enclose the drum, wherein the exterior shield is constructed of a material that substantially blocks the x-rays and defines a window that allows for the x-rays to pass through.

2. The portable x-ray backscattering imaging system of claim 1, comprising a controller in signal communication with the plurality of backscatter detectors.

3. The portable x-ray backscattering imaging system of claim 2, comprising an on-board positioning system in signal communication with the controller, wherein the on-board positioning system measures a horizontal displacement of the portable x-ray backscattering imaging system.

4. The portable x-ray backscattering imaging system of claim 3, wherein the on-board positioning system is selected from the group consisting of: an inertial measuring unit (IMU), a global positioning system (GPS), an optical encoder, at least one acoustic distance sensor, one or more linear encoders, and one or more encoder wheels.

5. The portable x-ray backscattering imaging system of claim 3, wherein the controller includes control logic for generating the backscatter image based on at least the horizontal displacement determined by the on-board positioning system, a density of the x-ray backscatter detected by the plurality of backscatter detectors, and a vertical scan movement of the radioactive source.

6. The portable x-ray backscattering imaging system of claim 2, comprising a display in signal communication with the controller.

7. The portable x-ray backscattering imaging system of claim 1, wherein the radioactive source is a gamma source.

8. The portable x-ray backscattering imaging system of claim 1, wherein the radioactive source is selected from the group consisting of: an alpha source, a beta source, and a neutron source.

9. The portable x-ray backscattering imaging system of claim 1, comprising at least one telescopic standoff for maintaining a fixed distance between the portable x-ray backscattering imaging system and an exterior surface of the object, and wherein the at least one telescopic standoff includes a motorized wheel.

10. The portable x-ray backscattering imaging system of claim 1, wherein the rotational speed of the drum is based on a specified vertical image contrast resolution of the backscatter image.

11. The portable x-ray backscattering imaging system of claim 1, wherein the scanning window is formed as an angle around the exterior shield.

12. The portable x-ray backscattering imaging system of claim 11, wherein the angle is based on a height of the backscatter image.

13. The portable x-ray backscattering imaging system of claim 1, wherein the radioactive source weighs less than about 28.3 grams.

14. The portable x-ray backscattering imaging system of claim 1, wherein the x-ray backscattering imaging system weighs between about 0.9 to about 2.2 kilograms.

15. A method of creating a backscatter image representing an object, comprising:
    generating x-rays by a radioactive source, wherein the radioactive source is connected to a drum, and wherein a container houses the radioactive source, the container constructed of a material that substantially blocks the x-rays generated by the radioactive source, and wherein the container defines a collimator having a length and an aperture opening;
    filtering a stream of x-rays generated by the radioactive source by the collimator such that the x-rays traveling substantially parallel with respect to the length of the collimator pass through the aperture;
    rotating the drum about an axis of rotation at a rotational speed;
    detecting backscatter radiation by a plurality of backscatter detectors, wherein the backscatter radiation is created as the x-rays generated by the radioactive source scatter back from the object;
    enclosing the drum by a portable exterior shield, wherein the exterior shield is constructed of a material that substantially blocks the x-rays and defines a window that allows for the x-rays to pass through; and
    generating the backscatter image on a display by a controller, wherein the controller is in signal communication with the plurality of backscatter detectors and the display.

16. The method of claim 15, comprising measuring a horizontal displacement of the portable x-ray backscattering imaging system by an on-board positioning system.

17. The method of claim 16, comprising generating the backscatter image based on at least one of a horizontal displacement determined by the on-board positioning system, a density of the x-ray backscatter detected by the plurality of backscatter detectors, and a vertical scan movement of the radioactive source.

18. The method of claim 15, wherein the rotational speed of the drum is based on a specified vertical image contrast resolution of the backscatter image.

19. A portable x-ray backscattering imaging system for creating a backscatter image representing an object, comprising:
- a drum rotating about an axis of rotation at a rotational speed;
- a radioactive source connected to the drum, radioactive source for generating x-rays;
- a plurality of backscattering detectors for detecting backscattering radiation created as the x-rays generated by the radioactive source scatter back from the object;
- a portable exterior shield to enclose the drum, wherein the exterior shield is constructed of a material that substantially blocks the x-rays and defines a window that allows for the x-rays to pass through; and
- at least one telescopic standoff for maintaining a fixed distance between the portable x-ray backscattering imaging system and an exterior surface of the object, and wherein the at least one telescopic standoff includes a motorized wheel.

* * * * *

UNITED STATES PATENT AND TRADEMARK OFFICE
CERTIFICATE OF CORRECTION

| | |
|---|---|
| PATENT NO. | : 9,658,173 B2 |
| APPLICATION NO. | : 14/447145 |
| DATED | : May 23, 2017 |
| INVENTOR(S) | : Gary Georgeson and Morteza Safai |

Page 1 of 1

It is certified that error appears in the above-identified patent and that said Letters Patent is hereby corrected as shown below:

In the Claims

Claim 1, Column 7, Line 39 reads:
"respect to the length of the collimator pass the aperture;"

Should read:
-- respect to the length of the collimator pass through the aperture; --

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*